United States Patent [19]

Jones

[11] 4,130,593
[45] Dec. 19, 1978

[54] ALKYLATION PROCESS UTILIZING THE HYDROCARBON PHASE FROM A REACTOR FOR CONDENSING A VAPOROUS DISTILLATION EFFLUENT

[75] Inventor: Richard H. Jones, South Euclid, Ohio

[73] Assignee: The Standard Oil Company, Cleveland, Ohio

[21] Appl. No.: 742,949

[22] Filed: Nov. 18, 1976

Related U.S. Application Data

[63] Continuation-in-part of Ser. No. 650,341, Jan. 19, 1976, abandoned.

[51] Int. Cl.² .............................................. C07C 23/02
[52] U.S. Cl. .......................... 260/683.48; 260/683.62; 260/683.4 F
[58] Field of Search ..................... 260/683.48, 683.43, 260/683.58, 683.62, 683.61, 683.42, 683.59

[56] References Cited

U.S. PATENT DOCUMENTS

| | | | |
|---|---|---|---|
| 2,905,735 | 9/1959 | Van Pool | 260/683.48 |
| 2,938,061 | 5/1960 | Smith | 260/683.48 |
| 2,949,494 | 8/1960 | Putney | 260/683.58 |
| 2,977,397 | 3/1961 | Putney | 260/683.48 |
| 2,986,590 | 5/1961 | Knoble et al. | 260/683.59 |
| 3,055,958 | 9/1962 | Webb, Jr. | 260/683.58 |
| 3,068,308 | 12/1962 | Stiles | 260/683.59 |
| 3,162,694 | 12/1964 | Beavon | 260/683.62 |
| 3,175,023 | 3/1965 | Gross et al. | 260/683.62 |
| 3,580,962 | 5/1971 | Moorer et al. | 260/683.62 |
| 3,925,501 | 12/1975 | Putney et al. | 260/683.48 |

FOREIGN PATENT DOCUMENTS

| | | |
|---|---|---|
| 966475 | 8/1964 | United Kingdom. |
| 1103259 | 2/1968 | United Kingdom. |
| 1165759 | 10/1969 | United Kingdom. |
| 1186965 | 4/1970 | United Kingdom. |
| 1202801 | 8/1970 | United Kingdom. |
| 1265525 | 3/1972 | United Kingdom. |

Primary Examiner—George Crasanakis
Attorney, Agent, or Firm—David J. Untener; Herbert D. Knudsen; Larry W. Evans

[57] ABSTRACT

In the process for the catalytic alkylation of isobutane with an olefin to produce alkylate, the liquid reactor effluent stream comprising a hydrocarbon mixture of alkylate, isobutane and inert alkanes is used to provide cooling to the various condensers in the alkylation process.

37 Claims, 5 Drawing Figures

4,130,593

ALKYLATION PROCESS UTILIZING THE HYDROCARBON PHASE FROM A REACTOR FOR CONDENSING A VAPOROUS DISTILLATION EFFLUENT

CROSS-REFERENCE TO RELATED APPLICATION

This application is a continuation-in-part of application Ser. No. 650,341, filed Jan. 19, 1976, now abandoned.

BACKGROUND OF THE INVENTION

Catalytic alkylation of isobutane is well known in the art, being the union of an olefin with isobutane in the presence of an acid catalyst to produce high octane branched chain hydrocarbons (alkylate) for use in aviation gasoline and motor fuel. Specifically, the olefin is combined with isobutane in the presence of an acid catalyst in a reactor and undergoes an exothermic reaction. The acid is then separated from the reactor effluent. After acid separation the reactor effluent then proceeds to a series of distillation columns to separate the inert alkanes, the unreacted isobutane for recycle, and to recover the alkylate. Treating is also performed on some of the effluent to remove residual acid and undesired reaction products. A variation of this process has been to use the vaporization of a portion of the reactor effluent to cool the reactor, see *Hydrocarbon Processing*, September, 1974, page 206.

There are several disadvantages with the present art alkylation process. First, large amounts of coolant, usually water or air, are necessary to condense the overhead streams from the distillation columns. Second, only a part of the reactor effluent is vaporized when cooling the reactor. This vapor is recovered as isobutane for recycle. The remaining liquid containing alkylate and a large amount of isobutane must then undergo treating to remove contaminants such as residue acid and then be distilled to separate the isobutane and alkylate. The larger this stream the larger the deisobutanizer column must be, and the more heat that is necessary to effect separation. The present invention reduces or eliminates these disadvantages while also making a substantial reduction in the energy required for the process.

SUMMARY OF THE INVENTION

The invention is in the process for the catalytic alkylation of isobutane with an olefin, comprising:

(a) contacting the olefin, a molar excess of isobutane and inert alkane in the liquid phase in the presence of an acid catalyst in a reactor to react substantially all of the olefin thus producing a liquid stream containing the acid catalyst and a hydrocarbon mixture containing alkylate, isobutane and inert alkanes;

(b) separating the acid catalyst from the hydrocarbon mixture;

(c) separating in a vapor-liquid separator the hydrocarbon mixture of (b) to obtain a liquid bottoms stream containing isobutane and alkylate and a vapor overhead stream containing isobutane and inert alkanes;

(d) compressing and condensing in a compressor effluent condenser the vapor overhead stream of (c) to produce a condensed overhead vapor stream;

(e) distilling in one or more distillation columns equipped with one or more column condensers, the liquid bottoms stream of (c) or the condensed overhead vapor stream of (d) to separate the isobutane from inert alkanes and alkylate, the improvement comprising:

vaporizing part of the hydrocarbon mixture of (b) to provide cooling to one or more condensers selected from the group consisting of column condensers or compressor effluent condensers.

In other words, the present invention relates to an improved continuous process for producing alkylate in which olefin and a molar excess of isobutane are reacted together in an alkylation zone in the presence of an acid to form a liquid effluent, the liquid effluent is removed from the alkylation zone, and liquid effluent so removed is subjected to processing to recover alkylate therefrom, the processing including vaporizing at least a portion of the liquid effluent to form vapors and thereafter condensing the vapors by cooling, the improvement in accordance with the present invention comprising cooling the vapors to be condensed by passing liquid effluent from the alkylation zone in indirect heat exchange with the vapors.

Using the present invention, the amount of isobutane that must be treated and recovered in the distillation column is greatly reduced, cooling water is no longer necessary for the distillation column overhead condenser, and the various distillation columns may be operated at substantially lower pressures, enhancing the separation process.

The central feature of the invention is the use of the reactor effluent to provide cooling to condensers in the alkylation process. By utilizing the effluent in this manner, substantial savings in operating expenses are realized, along with savings in capital investment for new units.

The invention is best understood by reference to the drawings.

DESCRIPTION OF THE DRAWINGS

Referring to FIG. 1, olefin and isobutane feed enter a reactor which contains the acid catalyst. The stream leaving the reactor contains acid catalyst, alkylate, isobutane and inert alkanes. This stream is then sent to an Acid Separator, where the acid catalyst is separated from the hydrocarbon mixture and returned to the Reactor. The resulting hydrocarbon mixture is then sent to one or more Condensers to supply necessary cooling. The use of this hydrocarbon mixture for cooling the condensers is the invention. The effluent from the Condensers then goes to the Vapor-Liquid Separator where isobutane is partially recovered as a vapor. By processing not shown in the drawing this vapor is compressed, condensed and returned to the Reactor. The liquid from the Separator then continues to the Deisobutanizer Column where isobutane is distilled overhead for recycle, and alkylate product is recovered as a bottoms stream.

Figure 1:
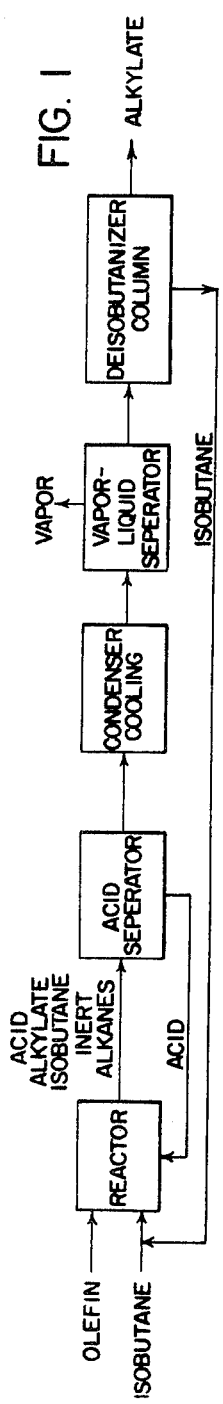
FIG. 1 shows a simplified block diagram of the invention.
Figure 2:
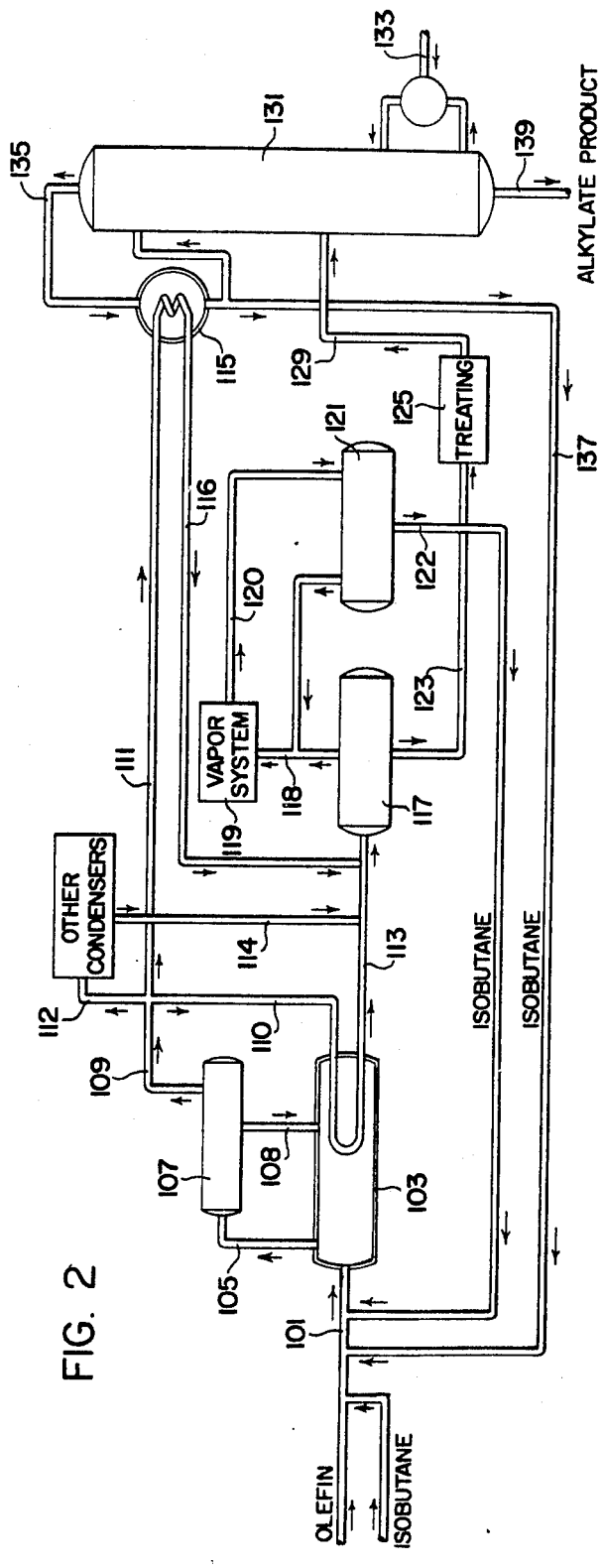
FIG. 2 shows the alkylation process of the present invention in greater detail.

Referring to the more detailed FIG. 2, olefin and isobutane are combined in line 101 and fed to a reactor 103 where the reactants are mixed with acid catalyst and reacted to form alkylate. The product leaves the reactor through line 105 to the acid separator 107. Here the acid is separated from the hydrocarbon mixture and returned to the reactor through line 108. The hydrocarbon mixture containing alkylate, isobutane and inert alkanes leaves the acid separator through line 109.

The hydrocarbon mixture goes to provide cooling in the condensers through lines 111 and 112. Specifically referring to line 111, it is seen how the present invention is applied to the deisobutanizer column. Hydrocarbon mixture is transmitted through line 111 to condenser 115 where at least part of the hydrocarbon mixture is vaporized to provide cooling in the condenser. The hydrocarbon mixture after providing cooling is transmitted through line 116 to the vapor-liquid separator 117. In the same manner cooling is supplied to other condensers such as other column condensers and compressor effluent condensers by taking the hydrocarbon mixture through line 112, vaporizing at least part of the hydrocarbon mixture in the condenser and transmitting the condenser effluent through line 114 to the vapor-liquid separator 117. In like manner the hydrocarbon mixture is used to cool the reactor through line 110, and is then transmitted through line 113 to the vapor liquid separator.

In the vapor-liquid separator 117 a vapor-liquid separation takes place. The vapor contains primarily isobutane and inert alkanes, and the liquid contains isobutane and alkylates. The vapors are transmitted through line 118 where the vapor is compressed and condensed in a vapor system 119. Normally in the vapor system 119 one or more columns are employed to remove the inert alkanes, such as propanes, from the isobutane. The isobutane stream is then sent through line 120 to a second vapor-liquid separator 121. The liquid isobutane stream is returned to the reactor through line 122 and the vapor is returned to the vapor system through line 118.

The liquid from the first vapor-liquid separator 117 containing isobutane and alkylate then proceeds through line 123 to the treating section 125 where residue acid and acidic compounds in the hydrocarbon mixture are removed. After treating, the liquid is transmitted through line 129 to the deisobutanizer column 131. Heat is applied to the column through line 133. Isobutane is distilled and exits the top of the column as a vapor in line 135. This vapor is condensed in the overhead condenser 115 and the condensed isobutane is then split for reflux to the column, and as recycle to the reactor through line 137. The alkylate product is recovered as a liquid bottoms stream through line 139.

Figure 3:
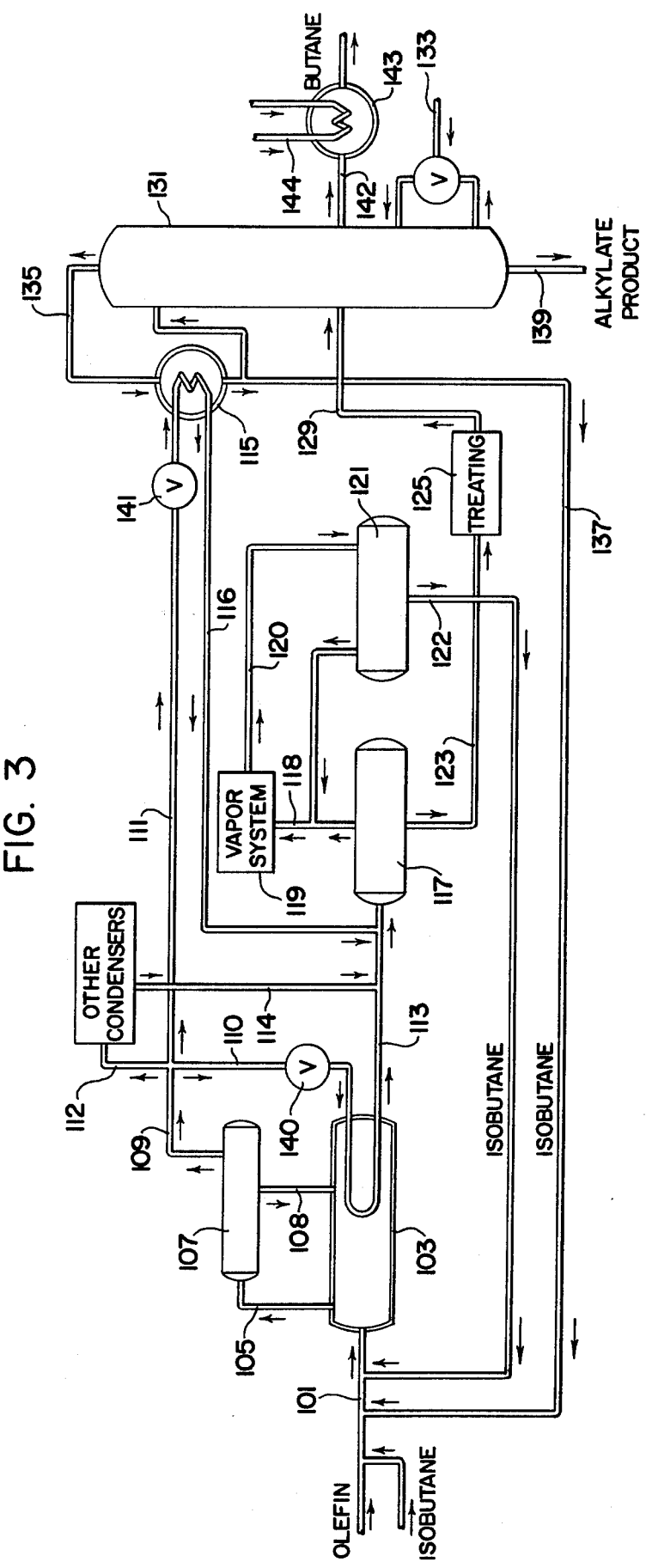
FIG. 3, which is similar to FIG. 2, shows an embodiment of the invention wherein pressure-reducing valves are used on the reactor effluent and a vaporous n-butane draw is removed from the deisobutanizer column.

FIG. 3, being similar to FIG. 2, shows another embodiment of the invention. The hydrocarbon mixture containing alkylate, isobutane and inert alkanes leaves the acid separator 107 through line 109. The hydrocarbon mixture then goes to provide cooling in the condensers through lines 111 and 112. Referring to line 111, a pressure reducing valve 141 is located in front of column condenser 115. This valve maintains the hydrocarbon mixture in line 111 as a liquid state. It also allows the downstream pressure of the hydrocarbon mixture going into condenser 115 and exiting in line 116 to be reduced. The pressure is reduced sufficiently to permit vaporization of the hydrocarbon mixture in condenser 115. Some vaporization may occur between valve 141 and condenser 115. A similar valve 140 is shown reducing the pressure of the hydrocarbon mixture in line 110 which provides cooling to reactor 103. Other pressure-reducing valves (not shown) may also be found in line 112 going to other condensers.

FIG. 3 also shows the deisobutanizer column 131 having a vaporous sidestream draw 142. Normal butane may be withdrawn from this column as a vapor in line 142 and condensed in column condenser 143. Typically, coolant is used in line 144 to provide cooling to condenser 143. However, the hydrocarbon mixture of line 112 with a suitable pressure reducing valve may also be used to provide this cooling. A n-butane sidestream draw may be used in the other embodiments of the present invention as well as the embodiment specifically illustrated in FIG. 3.

Figure 4:
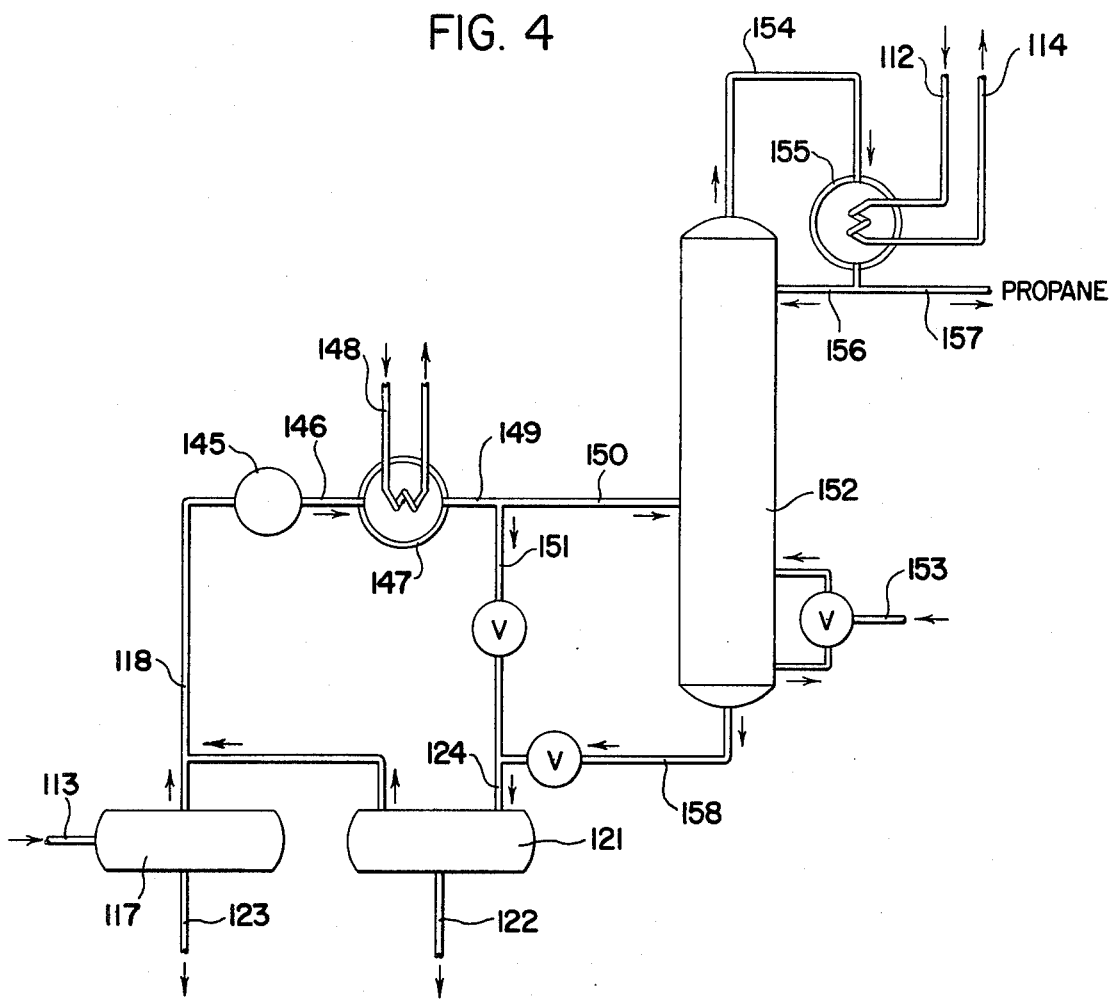
FIG. 4 shows in greater detail a vapor system which may be used as the vapor system illustrated in block in FIG. 2.

FIG. 4 shows a vapor system which may be employed as vapor system 119 in the apparatus of FIG. 2. The hydrocarbon mixture after being used as a coolant is transmitted through line 113 to vapor-liquid separator 117 wherein a vapor-liquid separation takes place. The vapors are transmitted through line 118 to compressor 145. The vapors are then compressed in the compressor and exit through line 146 to the compressor effluent condenser 147. Cooling is provided through line 148 to condenser 147 to condense the compressed vapor effluent. The cooling means may be cooling water but in another embodiment of the invention the hydrocarbon mixture of 112 with a suitable pressure reducing valve may also be used. The compressed condensed vapor effluent exits the condenser through line 149. A portion of this compressed condensed effluent is taken through line 150 to distillation column 152. The remainder is transmitted through line 151 to a second vapor-liquid separator 121, as also shown in FIG. 2.

Typically, distillation column 152 is a depropanizer column. Heat is applied to the column through line 153. Propane is distilled and exits the top of the column as a vapor in line 154. This vapor is condensed in the overhead condenser 155. In an embodiment of the invention, the hydrocarbon mixture of line 112, after pressure reduction is used to provide cooling to this condenser. The hydrocarbon mixture after providing cooling is transmitted through line 114 to the vapor-liquid separator 117 as shown in FIG. 2.

The condensed propane from condenser 155 is then split for reflux to the column through line 156 and also removed as a product through line 157. The bottoms product of this column containing mostly isobutane is transmitted through line 158 to the vapor-liquid separator 121.

Figure 5:
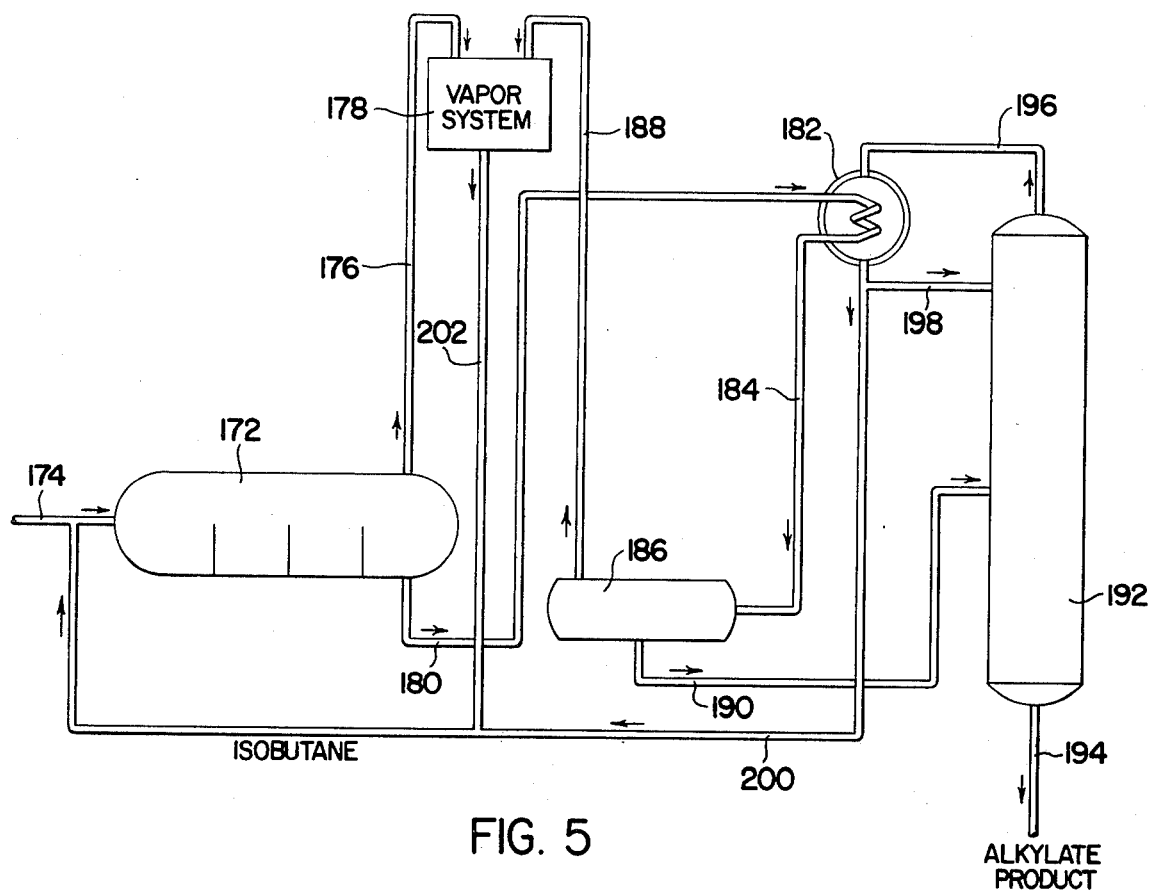
FIG. 5 shows still another embodiment of the present invention in accordance with which the inventive process is practiced in conjunction with an alkylation reactor producing both a liquid effluent and a vaporous effluent.

Still another embodiment of the present invention is illustrated in FIG. 5. In this embodiment, the alkylation reaction is accomplished in such a way that a vaporous effluent as well as a liquid effluent are produced by the alkylation reactor. Such processes are well-known as illustrated, for example, in U.S. Pat. No. 3,187,066 to Nathan, which was reissue as U.S. Pat. No. Re. 26,060.

As illustrated in FIG. 5, feed is passed into reactor 172 from conduit 174 where the alkylation reaction takes place. The vaporous reaction effluent produced is withdrawn from reactor 172 via conduit 176 and passed to a conventional vapor system 178 for the recovery of isobutane. Liquid reaction effluent exits reactor 172 via conduit 180 and passes through condenser 182 where it partially vaporizes. The partially vaporized liquid reactor effluent then passes through conduit 184 to vapor liquid separator 186 where vapor and liquid are separated from one another. Separated vapor travels via conduit 188 to vapor system 178 where it is processed along with the vaporous reactor effluent produced in reactor 172. The liquid stream passing out of vapor liquid separator 186 travels via conduit 190 to deisobutanizer 192 where it is separated. Alkylate product is recovered from deisobutanizer 192 via conduit 194 as column bottoms while isobutane-rich vapors are taken off deisobutanizer column 192 by means of conduit 196. Isobutane-rich vapors in conduit 196 pass through condenser 182 where they pass in indirect heat exchange relation with liquid reactor effluent obtained from reactor 172. Because of the cooling effect created by the vaporization of liquid reactor effluent in condenser 182, the isobutane-rich vapors in condenser 182 condense to an isobutane-rich liquid stream. A portion of this isobutane-rich liquid stream is sent to reflux via conduit 198 whereas the remainer is recycled to reactor 172 via conduit 200. Condensed isobutane recovered from vapor system 178 is also recycled to reactor 172 via conduit 202 as illustrated.

As appreciated by those skilled in the art, vapor system 178 normally includes a compressor for facilitating condensation of the vapor passed thereto. In accordance with the present invention, this compressor may if desired be a multi-stage compressor, and moreover the vapor fed from vapor/liquid separator 186 or similarly vapor-liquid separator 121 of FIG. 2 to this compressor may also be fed to the second or subsequent stages rather than the first stage of this compressor.

The advantages of the present invention are manifold. First, because the feed to the deisobutanizer is reduced, the volume of the stream treated is reduced. Typically this treating consists of a caustic wash followed by a water wash. The size of the caustic treater is decreased effecting a savings in capital cost for the equipment required. A second advantage is the size of the deisobutanizer column. Because a larger amount of isobutane is vaporized in the reactor effluent, less has to be recovered in the distillation column. This means a reduction in both the size of the column and the heat input necessary for operation. Still another advantage can be found by using the effluent stream as the cooling medium for the overhead condensers located on the deisobutanizer and other distillation columns in the process, such as a depropanizer and debutanizer. The use of the effluent stream allows lower operating temperatures and pressures for these columns than could be realized using water or air. Also, elimination of water as a coolant means that the associated utilities, such as a cooling tower, can be decreased in size or eliminated. This reduction in operating temperature and pressure of the columns serves to increase the relative volatility of the key components, meaning less energy input in the form of heat is necessary to perform the separation required. Thus a unique savings is made in utilities because the water used to condense the overhead is no longer necessary, and the heat to the tower for separation is reduced.

PREFERRED DESCRIPTION OF EMBODIMENT

In the preferred concept of this invention the reactor effluent, after acid separation, is sent to the overhead condensers on the distillation columns in the process. This concept is preferred because lower temperatures can be achieved using the reactor effluent than by using cooling water. With lower temperatures and pressures in the columns the separation process is greatly enhanced. If more than one condenser is cooled by the effluent stream, they may be connected in either parallel or series fashion. It is preferred that they be connected in parallel to minimize capital costs.

Typically at least two distillation columns are present, a deisobutanizer for separating isobutane from the alkylate product, and a depropanizer to remove the lighter propane from the isobutane. In some cases a third column for separating butane from alkylate is also involved.

A variant of this invention is to use the reactor effluent stream in other locations in the process that requires cooling. This may be in addition to or exclusive of cooling the overhead condensers on the distillation columns. Condensers are normally found in other locations om distillation columns, such as cooling the liquid bottoms product or condensing a vapor sidestream draw. For example, instead of having a debutanizer column, butane may be removed from the process as a vapor taken from some point in the deisobutanizer column. The reactor effluent may be used to condense this vapor to produce a liquid butane product.

Another variant is to use the reactor effluent to cool the compressed vapor effluent stream from the first vapor-liquid separator. These compressed vapors containing isobutane and some inert alkanes must be condensed before they are sent to further distillation columns to remove the inert alkanes or back to the reactor as recycle isobutane. The reactor effluent may be used in the vapor compressor effluent condenser, thereby eliminating another usage of cooling water.

It is anticipated that this invention may be used in any catalytic alkylation process involving an acid catalyst. The acid catalysts that may be used are known in the art, including but not limited to sulfuric and hydrofluoric acid. Preferred in the present invention is the use of sulfuric acid catalyst.

The reaction conditions and parameters are unchanged by this invention. Normally the reactor is operated between 1-200 psig, and a temperature between $-10°$ to $50°$ C. The olefin feed to the alkylation process is also known in the art being typically a hydrocarbon of 2-5 carbons and is not affected by the present invention. Normally the composition of the olefin feed depends on the specific application, but may comprise propylene, butylenes or amylenes. The olefin feed may also contain various inert alkanes, such as propane and butane. The olefin is mixed with isobutane either before going to the reactor or in the reactor. Normally the higher the ratio of isobutane to olefin in the feed stock the greater the yield of alkylate. This external ratio is usually about 5:1 but can be 15:1 or higher. The present invention takes advantage of this ratio by recovering isobutane for recycle in a more efficient and less costly manner than the present art. By using this invention in existing units this ratio can be increased, thereby improving the octane of the product without being limited by the size of the deisobutanizer.

As indicated above, the hydrocarbon mixture being used to provide cooling may be passed through a pressure-reducing valve prior to its entry into the condensers if desired. The pressure is reduced sufficiently to permit vaporization and affect greater cooling in the condenser. The pressure may be reduced to a pressure of 1 psia to about 50 psia. It is preferred to reduce this pressure to 3 psig to about 5 psig.

SPECIFIC EMBODIMENT

Example 1 and Comparative Example A

A computer simulation was made of an alkylation process as depicted in the Hydrocarbon Processing reference of September, 1974, page 206. Sulfuric acid was used as the acid catalyst. The reactant feed to both examples is given in Table I in barrels per stream day, being a comination of isobutane, butylene, and inert alkanes.

TABLE I

| Reactant Feed To Alkylation Process | |
|---|---|
| Isobutane | 3830 |
| Butylene | 3090 |
| Inert Alkanes | 1385 |

For comparison, the amount of product and its octane number of 98.5 was held constant for both examples. The isobutane in the reaction zone was held at 80 percent of the total feed plus recycle. Due to the larger amounts of inert alkanes that are recycled in the effluent refrigeration stream in the present invention, this has the effect of increasing the isobutane/olefin ratio in the reactor. The other operating conditions of the reactor was the same for both examples.

Comparative Example A shows the present art. The reactor effluent after acid separation was used to cool the reactor. After cooling, the effluent stream was sent to the first vapor-liquid separator. The liquid from this separator constituted the stream that was treated and sent as feed to the deisobutanizer column. Cooling water was used as the cooling medium in the overhead condenser of this column.

In Example 1, showing the present invention, the reactor effluent, in addition to cooling the reactor, was sent in a parallel manner to the overhead condenser of the deisobutanizer. After cooling, the reactor effluent was collected in the first vapor-liquid separator. Table II shows the results of these two examples. Quantities shown are barrels per stream day.

TABLE II

| Comparison of Art Alkylation With Invention | | |
|---|---|---|
| | Comparative Example A | Example 1 Invention |
| 1. IC$_4$ in feed | 3,830 | 3,830 |
| 2. IC$_4$ olefin ratio in reactor | 15.9 | 18.2 |
| 3. IC$_4$ in vapor from separator | 25,945 | 52,594 |
| 4. Deisobutanizer | | |
| IC$_4$ in feed | 26,999 | 15,741 |
| IC$_4$ in overhead product | 26,602 | 15,344 |
| condenser duty* | 54.4 | 40.8 |
| reboiler duty* | 63.0 | 47.2 |
| column diameter (ft.) | 11.3 | 9.8 |

*MM BTU/hr.

As shown in Table II, far more of the isobutane (IC$_4$) contained in the reactor effluent is vaporized, allowing for a more efficient recovery. The present invention reduces the amount of isobutane feed to the deisobutanizer by more than 40 percent, thereby reducing both the size of this column and the utilities required for distillation.

EXAMPLE 2

Using the same feed composition and reactor conditions of example 1, example 2 shows the effect of cooling the overhead condenser on the deisobutanizer column with reactor effluent only. Cooling water was completely eliminated, and the refrigerant effect of the reactor effluent allowed the pressure in the deisobutanizer column to be reduced from 150 psig to 17 psig. This reduction in pressure improves separation, and allowed the amount of heat needed for operation to be reduced to 35.7 MM BTU/hr., more than 40 percent less heat than was required for the present art in Comparative Example A.

I claim:

1. A process for the catalytic alkylation of isobutane with an olefin comprising the steps of:
   (a) contacting said olefin with a molar excess of isobutane and inert alkanes in the presence of an acid catalyst in a reactor to form a reactor effluent containing alkylate, isobutane, acid catalyst and inert alkanes;
   (b) separating said acid catalyst from said reactor effluent to form a hydrocarbon mixture;
   (c) effecting a liquid vapor separation on said hydrocarbon mixture to obtain a liquid bottoms stream containing isobutane and alkylate and an overhead vapor stream containing isobutane and intert alkanes;
   (d) distilling said liquid bottoms stream to separate alkylate product as a liquid bottoms product and isobutane as a vaporous distillation effluent;
   (e) passing a first portion of said hydrocarbon mixture from step (b) as a cooling effluent in indirect heat exchange with said vaporous distillation effluent to condense said isobutane and to vaporize a portion of said cooling effluent; and
   (f) passing said cooling effluent from step (e) to said liquid vapor separation of step (c).

2. The process of claim 1 wherein said portion of said hydrocarbon mixture from step (b) is vaporized by reducing the pressure of said hydrocarbon mixture prior to step (e).

3. The process of claim 1 including the step of removing residual acid and impurities from said liquid bottoms stream of (c) prior to distilling said stream.

4. The process of claim 1 wherein said condensed isobutane of (e) is recycled to said reactor.

5. The process of claim 1 including the steps of compressing and condensing said overhead vapor stream of (c) to produce liquid isobutane in said condensed overhead vapor stream.

6. The process of claim 5 including the step of separating said liquid isobutane from said condensed overhead vapor stream in a vapor-liquid separator.

7. The process of claim 6 wherein said liquid isobutane is recycled to said reactor.

8. The process of claim 5 including the step of utilizing a second portion of said hydrocarbon mixture from step (b) as a second cooling effluent to effect the condensation of said overhead vapor stream by passing said second cooling effluent in indirect heat exchange with said overhead vapor stream.

9. The process of claim 5 including the step of distilling a portion of said condensed vapor stream to remove inert alkanes as a vaporous alkane fraction and condensing said vaporous alkane fraction from the alkane distillation by passing said vaporous alkane fraction in indirect heat exchange with a second portion of said cooling effluent.

10. The process of claim 9 wherein said inert alkane fraction is propane.

11. The process of claim 1 wherein said liquid bottoms stream of (c) additionally contains normal butane and wherein the distillation of said liquid bottoms stream of (c) includes the removal of normal butane as a vaporous sidestream and condensing said vaporous sidestream by passing it in indirect heat exchange with a second portion of said hydrocarbon mixture from step (b).

12. In a continuous process for producing alkylate in which olefin and a molar excess of isobutane are reacted together in an alkylation zone in the presence of an acid catalyst to form a liquid reaction effluent, said liquid reaction effluent is separated into an acid catalyst phase and a hydrocarbon mixture, and said hydrocarbon mixture is subjected to fractionation to recover alkylate therefrom, said fractionation including separating said hydrocarbon mixture to form a vaporous fraction and thereafter condensing said vaporous fraction by cooling, the improvement wherein said vaporous fraction is cooled by passing a portion of said hydrocarbon mixture from said alkylation zone in indirect heat exchange with said vaporous fraction.

13. The process of claim 12 wherein said portion of said hydrocarbon mixture passed in indirect heat exchange with said vaporous fraction is partially vaporized.

14. The process of claim 13 wherein the pressure of said hydrocarbon mixture passed in indirect heat exchange with said vaporous fraction is reduced prior to said indirect heat exchange sufficiently to permit additional vaporization of said hydrocarbon mixture during said cooling.

15. The process of claim 15 wherein said hydrocarbon mixture passed in indirect heat exchange with said vaporous fraction passes directly from said alkylation zone through a pressure reduction valve to indirect heat exchange relation with said vaporous fraction.

16. The process of claim 14 wherein fractionation of said hydrocarbon mixture includes distilling a liquid stream from said hydrocarbon mixture.

17. The process of claim 14 wherein fractionation of said hydrocarbon mixture includes distilling a liquid stream from said hydrocarbon mixture in a deisobutanizer to produce isobutane-rich vapors and alkylate-rich liquid bottoms, said isobutane-rich vapors being cooled and condensed by indirect heat exchange with said hydrocarbon mixture.

18. The process of claim 17 wherein fractionation of said hydrocarbon mixture includes partially vaporizing said hydrocarbon mixture to form a liquid stream and a vapor stream, said liquid stream being fed to said deisobutanizer.

19. The process of claim 18 wherein said hydrocarbon mixture from said alkylation zone is separated into a first portion and a second portion, said first portion being passed in indirect heat exchange with the reaction mixture in said alkylation zone, said second portion being passed in indirect heat exchange with said vaporous stream to effect said cooling, said first and second portions being mixed with one another following said indirect heat exchange and passed to a vapor/liquid separator for separating said liquid stream and said vapor stream from one another.

20. The process of claim 14 wherein fractionation of said hydrocarbon mixture to recover alkylate includes recovering propane in vapor form by distillation, the vaporous propane being condensed by cooling, cooling of said vapors propane being accomplished by passing said hydrocarbon mixture from said alkylation zone in indirect heat exchange with said vaporous propane.

21. The process of claim 14 wherein fractionation of said hydrocarbon mixture includes at least partially vaporizing said hydrocarbon mixture to form a liquid phase and a vapor phase, said vapor phase being separated from said liquid phase and cooling to condense said vapor phase by passing said hydrocarbon mixture from said alkylation zone in indirect heat exchange with said vapor phase.

22. The process of claim 12 wherein the olefin is a hydrocarbon of 2-5 carbons.

23. The process of claim 12 wherein the olefin is propylene.

24. The process of claim 12 wherein the olefin is selected from the group consisting of butylenes or amylenes.

25. The process of claim 12 wherein the acid catalyst is sulfuric acid.

26. The process of claim 12 wherein said acid catalyst is hydrofluoric acid.

27. A process for catalytic alkylation of isobutane with an olefin comprising the steps of:
(a) contacting said olefin with a molar excess of isobutane and inert alkanes in the presence of an acid catalyst in a reactor to form a reactor effluent containing alkylate, isobutane, acid catalyst and inert alkanes;
(b) separating said acid catalyst from said reactor effluent to form a hydrocarbon mixture;
(c) effecting a liquid vapor separation on said hydrocarbon mixture to obtain a liquid bottoms stream containing isobutane and alkylate and an overhead vapor stream containing isobutane and inert alkanes;
(d) compressing and condensing said overhead vapor stream to produce a condensed overhead vapor stream;
(e) distilling a portion of said condensed overhead vapor stream to separate isobutane as liquid bottoms and inert alkane as a vaporous fraction;
(f) passing a portion of said hydrocarbon mixture from step b as a cooling effluent in indirect heat exchange with said vaporous fraction of step (e) to condense the inert alkane therein and to vaporize a portion of said cooling effluent; and thereafter
(g) passing said cooling effluent from step (f) to the liquid vapor separation of step (c).

28. The process of claim 27 wherein the inert alkane is propane.

29. In the process for the catalytic alkylation of isobutane with an olefin, comprising:
(a) contacting the olefin, a molar excess of isobutane and inert alkane in the liquid phase in the presence of an acid catalyst in a reactor to react substantially all of the olefin thus producing a liquid stream containing the acid catalyst and a hydrocarbon mixture containing alkylate, isobutane and inert alkanes;
(b) separating the acid catalyst from the hydrocarbon mixture;
(c) separating in a vapor-liquid separator said hydrocarbon mixture of (b) to obtain a liquid bottoms stream containing isobutane and alkylate and a vapor overhead stream containing isobutane and inert alkanes;

(d) compressing and condensing in a compressor effluent condenser the vapor overhead stream of (c) to produce a condensed overhead vapor stream;

(e) distilling in one or more distillation columns equipped with one or more column condensers, the liquid bottoms stream of (c) to separate alkylate product from isobutane and the condensed overhead vapor stream of (d) to separate the isobutane from inert alkanes, the improvement comprising; vaporizing a part of the hydrocarbon mixture of (b) in direct heat exchange to provide cooling to one or more condensers utilized in steps (d) and (e).

30. The process of claim 29 wherein the column condenser is a condenser on an overhead vapor stream of the column.

31. The process of claim 29 wherein the olefin is a hydrocarbon of 2–5 carbons.

32. The process of claim 29 wherein the olefin is propylene.

33. The process of claim 29 wherein the olefin is selected from the group consisting of butylenes or amylenes.

34. The process of claim 29 wherein the acid catalyst is sulfuric acid.

35. The process of claim 29 wherein the acid catalyst is hydrofluoric acid.

36. The process of claim 29 wherein the column condenser is a condenser on an overhead vapor stream of a deisobutanizer column.

37. The process of claim 29 wherein the column condenser is a condenser on an overhead vapor stream of a depropanizer column.

* * * * *